United States Patent
Murayama

(10) Patent No.: US 9,789,459 B2
(45) Date of Patent: Oct. 17, 2017

(54) NUCLEIC ACID AMPLIFICATION REACTION VESSEL AND NUCLEIC ACID AMPLIFICATION REACTION APPARATUS

(71) Applicant: Seiko Epson Corporation, Tokyo (JP)

(72) Inventor: Toshiro Murayama, Fujimi (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 14/625,146

(22) Filed: Feb. 18, 2015

(65) Prior Publication Data
US 2015/0231591 A1 Aug. 20, 2015

(30) Foreign Application Priority Data

Feb. 20, 2014 (JP) .................................. 2014-030362

(51) Int. Cl.
*B01J 19/00* (2006.01)
*C12Q 1/68* (2006.01)

(52) U.S. Cl.
CPC .... *B01J 19/0046* (2013.01); *B01J 2219/0031* (2013.01); *B01J 2219/00283* (2013.01); *B01J 2219/00344* (2013.01); *B01J 2219/00495* (2013.01); *B01J 2219/00585* (2013.01); *B01J 2219/00599* (2013.01); *B01J 2219/00722* (2013.01); *C12Q 1/686* (2013.01)

(58) Field of Classification Search
CPC .............................. B01J 19/0046; B01J 19/00
See application file for complete search history.

(56) References Cited

U.S. PATENT DOCUMENTS

| | | |
|---|---|---|
| 6,515,743 B1 | 2/2003 | Hayashi et al. |
| 6,875,602 B2 | 4/2005 | Gutierrez |
| 8,932,833 B2 | 1/2015 | Yamaguchi et al. |
| 9,206,385 B2 | 12/2015 | Koeda et al. |
| 9,463,462 B2 | 10/2016 | Murayama et al. |
| 2002/0155475 A1 | 10/2002 | Vischer |
| 2007/0009382 A1 | 1/2007 | Bedingham et al. |
| 2007/0099189 A1 | 5/2007 | Gomez-Elvira Rodriguez et al. |
| 2008/0176290 A1 | 7/2008 | Joseph et al. |
| 2009/0317898 A1 | 12/2009 | Hanafusa et al. |

(Continued)

FOREIGN PATENT DOCUMENTS

| | | |
|---|---|---|
| CN | 101218030 A | 7/2008 |
| JP | 2004-508837 A | 3/2004 |

(Continued)

OTHER PUBLICATIONS

Qiagen OneStep RT-PCR Kit, Quick-Start Protocol, published Jan. 2011, pp. 1-4.

(Continued)

*Primary Examiner* — Nathan Bowers
*Assistant Examiner* — Lydia Edwards
(74) *Attorney, Agent, or Firm* — Harness, Dickey & Pierce, P.L.C.

(57) ABSTRACT

A nucleic acid amplification reaction vessel includes a first inner wall, and a second inner wall that is arranged opposite to the first inner wall, in which a distance between the first inner wall and the second inner wall is a length in which a nucleic acid amplification reaction solution comes into contact with both the first inner wall and the second inner wall when the nucleic acid amplification reaction solution is poured.

8 Claims, 9 Drawing Sheets

(56) References Cited

U.S. PATENT DOCUMENTS

| | | |
|---|---|---|
| 2010/0279392 A1 | 11/2010 | Kodama et al. |
| 2010/0285989 A1 | 11/2010 | Huo et al. |
| 2011/0183378 A1 | 7/2011 | Takagi et al. |
| 2011/0189660 A1 | 8/2011 | Koeda |
| 2011/0256590 A1 | 10/2011 | Koeda |
| 2012/0122160 A1 | 5/2012 | Saito et al. |
| 2012/0145260 A1 | 6/2012 | Koeda |
| 2012/0225001 A1 | 9/2012 | Koeda |
| 2012/0301367 A1 | 11/2012 | Koeda |
| 2013/0130229 A1 | 5/2013 | Sugiyama et al. |
| 2013/0157276 A1 | 6/2013 | Edvinsson et al. |
| 2013/0210081 A1 | 8/2013 | Koeda |
| 2013/0330818 A1* | 12/2013 | Koeda .................. C12M 41/12 435/303.1 |
| 2014/0273201 A1 | 9/2014 | Saito et al. |
| 2015/0231591 A1 | 8/2015 | Murayama |
| 2015/0232922 A1 | 8/2015 | Murayama |
| 2015/0273472 A1 | 10/2015 | Murayama |
| 2015/0343447 A1 | 12/2015 | Togashi et al. |

FOREIGN PATENT DOCUMENTS

| | | |
|---|---|---|
| JP | 2005-034121 A | 2/2005 |
| JP | 2008-012490 A | 1/2008 |
| JP | 2008-526216 A | 7/2008 |
| JP | 2009-136250 A | 6/2009 |
| JP | 2009-207459 A | 9/2009 |
| JP | 2010-516281 A | 5/2010 |
| JP | 2011-174734 A | 9/2011 |
| JP | 2012-023987 A | 2/2012 |
| JP | 2012-115208 A | 6/2012 |
| JP | 2012-179002 A | 9/2012 |
| JP | 2013-217699 A | 10/2013 |
| JP | 2013-252092 A | 12/2013 |
| JP | 2014-176304 A | 9/2014 |
| WO | WO-02-22878 | 3/2002 |
| WO | WO-2006-074217 A2 | 7/2006 |
| WO | WO-2006-106867 A1 | 10/2006 |
| WO | WO-2008-091626 A1 | 7/2008 |
| WO | WO-2008-146754 A1 | 12/2008 |
| WO | WO-2012-073484 A1 | 6/2012 |

OTHER PUBLICATIONS

Yeh et al., "Quantification and genotyping of hepatitis B virus in a single reaction by real-time PCR and melting curve analysis," Journal of Hepatology, 2004, vol. 41, pp. 659-666.

* cited by examiner

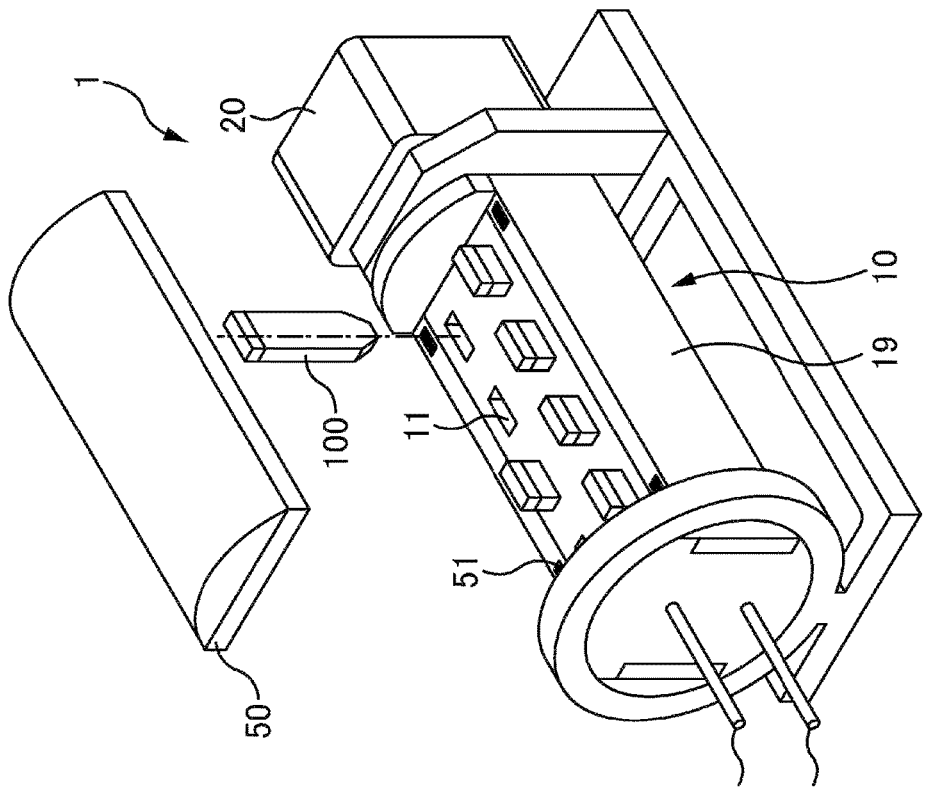
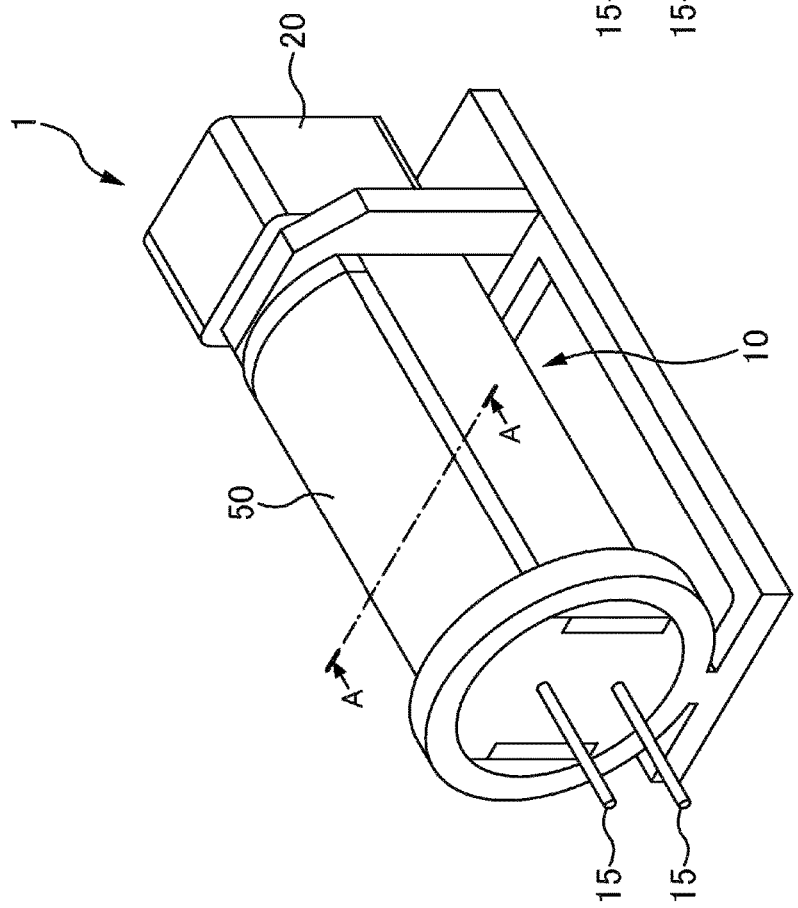
FIG. 1B
FIG. 1A

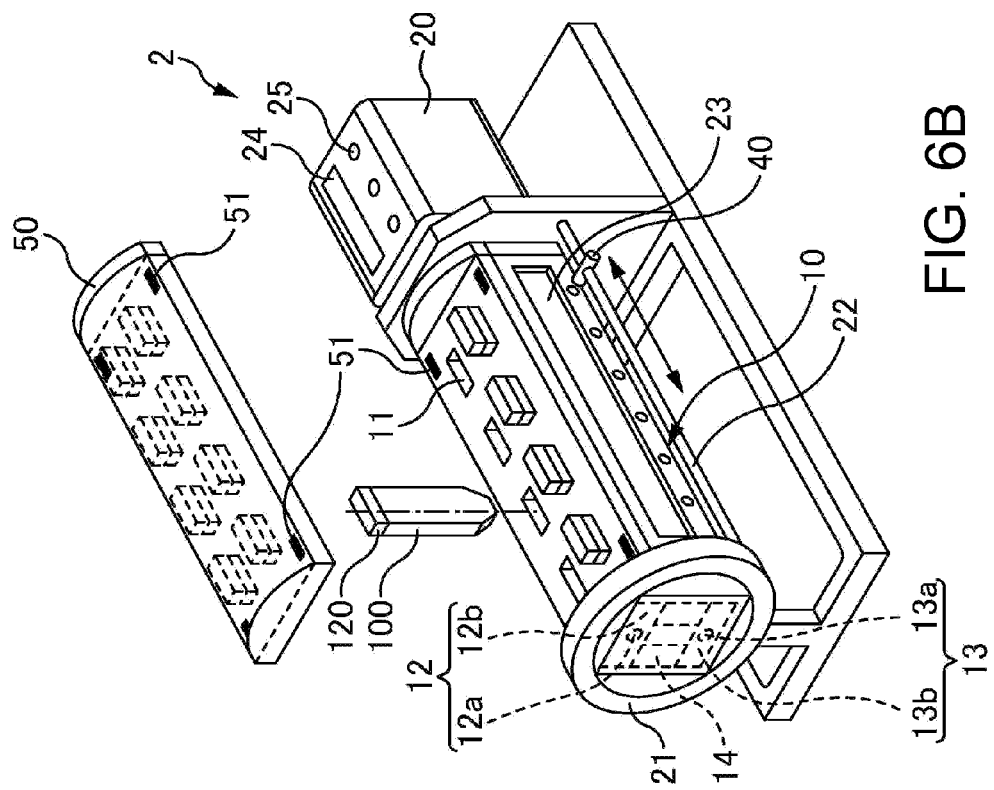
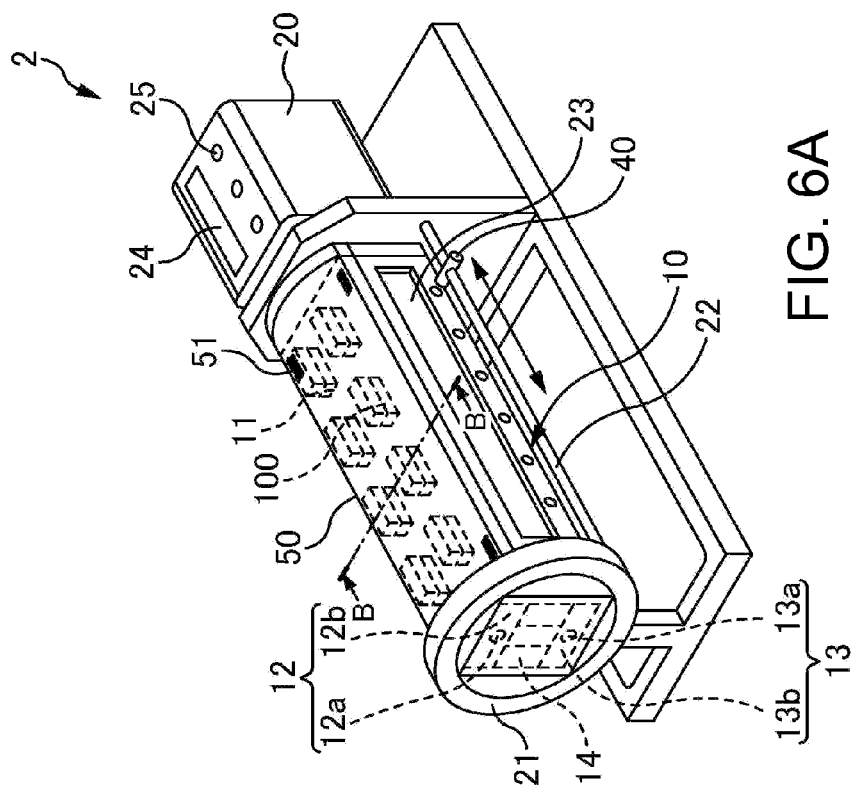
FIG. 6A
FIG. 6B

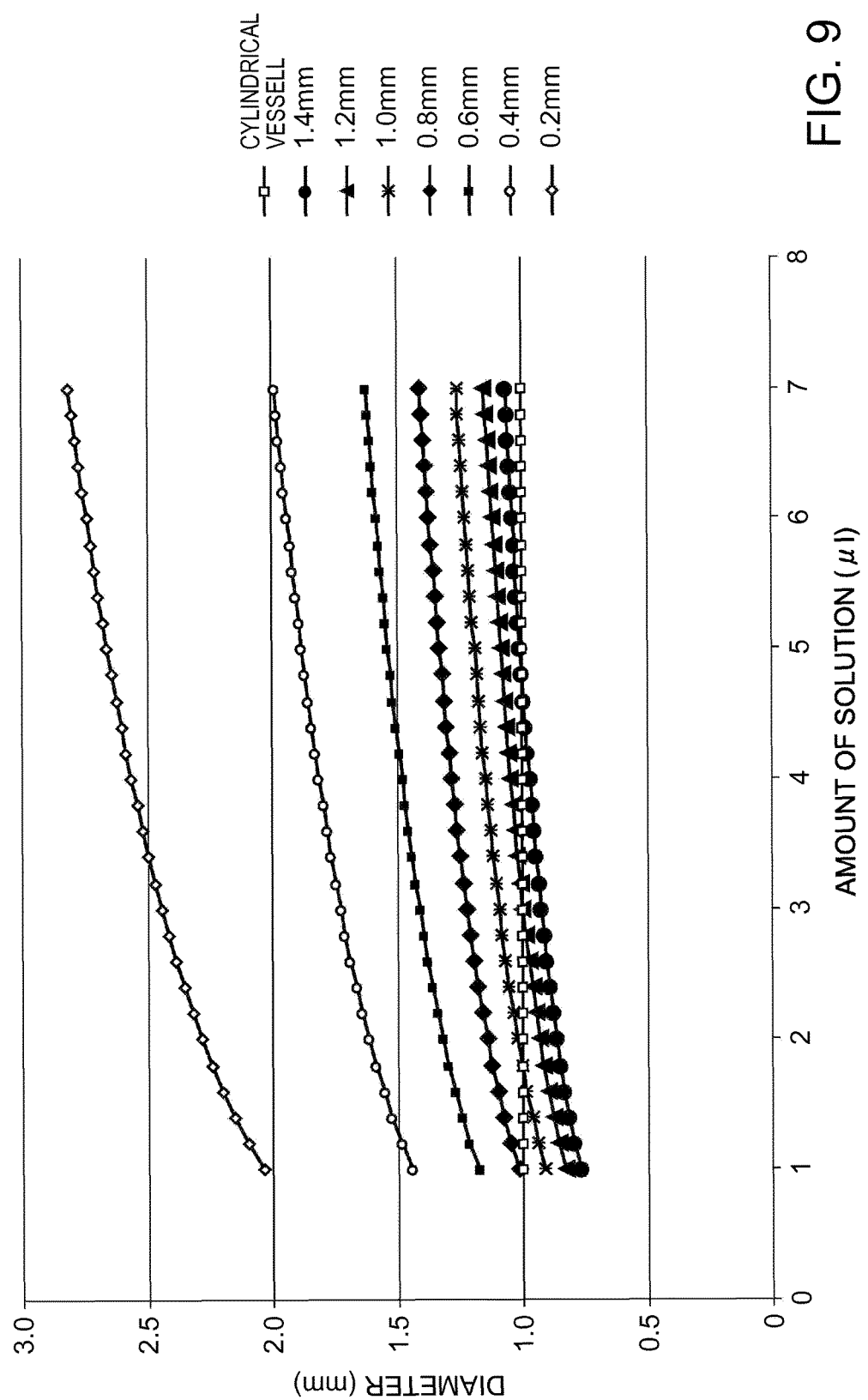

NUCLEIC ACID AMPLIFICATION REACTION VESSEL AND NUCLEIC ACID AMPLIFICATION REACTION APPARATUS

BACKGROUND

1. Technical Field

The present invention relates to a nucleic acid amplification reaction vessel and a nucleic acid amplification reaction apparatus.

2. Related Art

As a method of amplifying nucleic acid at a high speed, a method of generating a thermal cycle at a high speed at the temperature of a nucleic acid amplification reaction solution by putting an oil and a small amount of nucleic acid amplification reaction solution in a cylindrical nucleic acid amplification reaction vessel, while maintaining one end of the vessel at a high temperature and the other end thereof at a low temperature, rotating the vessel such that a state in which the one end is on a lower side in a vertical direction so that the reaction solution is located in the oil at a high temperature and a state in which the other end is on the lower side in the vertical direction so that the reaction solution is located in the oil at a low temperature are alternatively switched is known (for example, refer to JP-A-2012-115208).

The cylindrical reaction vessel is used in a nucleic acid amplification reaction apparatus disclosed in JP-A-2012-115208 and the diameter of the droplets of the nucleic acid amplification reaction solution is smaller than the diameter of the reaction vessel. Thus, the nucleic acid amplification reaction solution has a two-dimensional degree of freedom in a plane perpendicular to the longitudinal direction of the reaction vessel. Accordingly, the droplets of the nucleic acid amplification reaction solution fall obliquely with respect to the gravitational direction or fall perpendicularly with respect to the gravitational direction, which causes an uneven falling speed of the droplets of the nucleic acid amplification reaction solution. Thus, it is not easy to strictly control the amount of the nucleic acid amplification reaction solution to be heated. When the amount of the nucleic acid amplification reaction solution to be heated is not sufficiently controlled, there is a possibility that the amount of nucleic acid to be amplified becomes uneven.

SUMMARY

An advantage of some aspects of the invention is that nucleic acid is stably amplified.

An aspect of the invention is directed to a nucleic acid amplification reaction vessel including a first inner wall, and a second inner wall that is arranged opposite to the first inner wall, in which a distance between the first inner wall and the second inner wall is a length in which a nucleic acid amplification reaction solution comes into contact with both the first inner wall and the second inner wall when the nucleic acid amplification reaction solution is poured. The first inner wall and the second inner wall are preferably flat. When an amount of the nucleic acid amplification reaction solution is 1 µl to 7 µl, the distance may be 0.2 mm to 1.4 mm. A center portion of a bottom portion of the nucleic acid amplification reaction vessel may protrude outward.

Another aspect of the invention is directed to a nucleic acid amplification reaction apparatus including the nucleic acid amplification reaction vessel according to the aspect of the invention, a first heating section that heats a first region of the nucleic acid amplification reaction vessel, and a driving mechanism that switches arrangement of the first region, a second region of the nucleic acid amplification reaction vessel, and the first heating section into a first arrangement or a second arrangement, in which the first arrangement is an arrangement in which the first region is on a lower side of the second region with respect to a gravitational direction and the second arrangement is an arrangement in which the second region is on a lower side of the first region with respect to the gravitational direction. When the nucleic acid amplification reaction vessel is mounted in amounting section, the nucleic acid amplification reaction apparatus may include a second heating section that heats the second region, the first heating section may heat the first region to a first temperature, and the second heating section may heat the second region to a second temperature which is different from the first temperature.

According to the aspects of the invention, it is possible to provide a nucleic acid amplification reaction vessel and a nucleic acid amplification reaction apparatus capable of more stably duplicating nucleic acid in a method of conducting a nucleic acid amplification reaction at a high speed by moving a nucleic acid amplification reaction solution in an oil having different temperature regions.

BRIEF DESCRIPTION OF THE DRAWINGS

The invention will be described with reference to the accompanying drawings, wherein like numbers reference like elements.

FIGS. 1A and 1B are perspective views of a nucleic acid amplification reaction apparatus according to an embodiment, of which FIG. 1A shows a state in which a lid is closed and FIG. 1B shows a state in which the lid is opened.

FIGS. 3A and 3B are cross-sectional views of a nucleic acid amplification reaction vessel according to the embodiment, of which FIG. 3A is a cross-sectional view of the nucleic acid amplification reaction vessel in a parallel direction with respect to a first inner wall and a second inner wall that are opposite to each other and FIG. 3B is a cross-sectional view of the nucleic acid amplification reaction vessel in a direction orthogonal with respect to the first inner wall and the second inner wall.

FIGS. 4A and 4B are cross-sectional views schematically showing a cross section of the main body of the nucleic acid amplification reaction apparatus according to the embodiment taken along line A-A in FIG. 1A, of which FIG. 4A shows a first arrangement and FIG. 4B shows a second arrangement.

FIGS. 6A and 6B are perspective views of a nucleic acid amplification reaction apparatus according to a modification example, of which FIG. 6A shows a state in which a lid is closed and FIG. 6B shows a state in which the lid is opened.

FIG. 9 is a graph showing ratios of projection diameters of droplets in the nucleic acid amplification reaction vessel according to the embodiment of the invention to projection diameters of droplets in a cylindrical nucleic acid amplification reaction vessel.

DESCRIPTION OF EXEMPLARY EMBODIMENTS

Hereinafter, a preferred embodiment of the invention will be described in the following procedure using the drawings. It should be noted that the embodiment described below does not unreasonably limit the content of the invention described in the appended claims. Further, all of the configurations described below are not necessarily essential constituent requirements of the invention.

1. Embodiment

Figure 2:
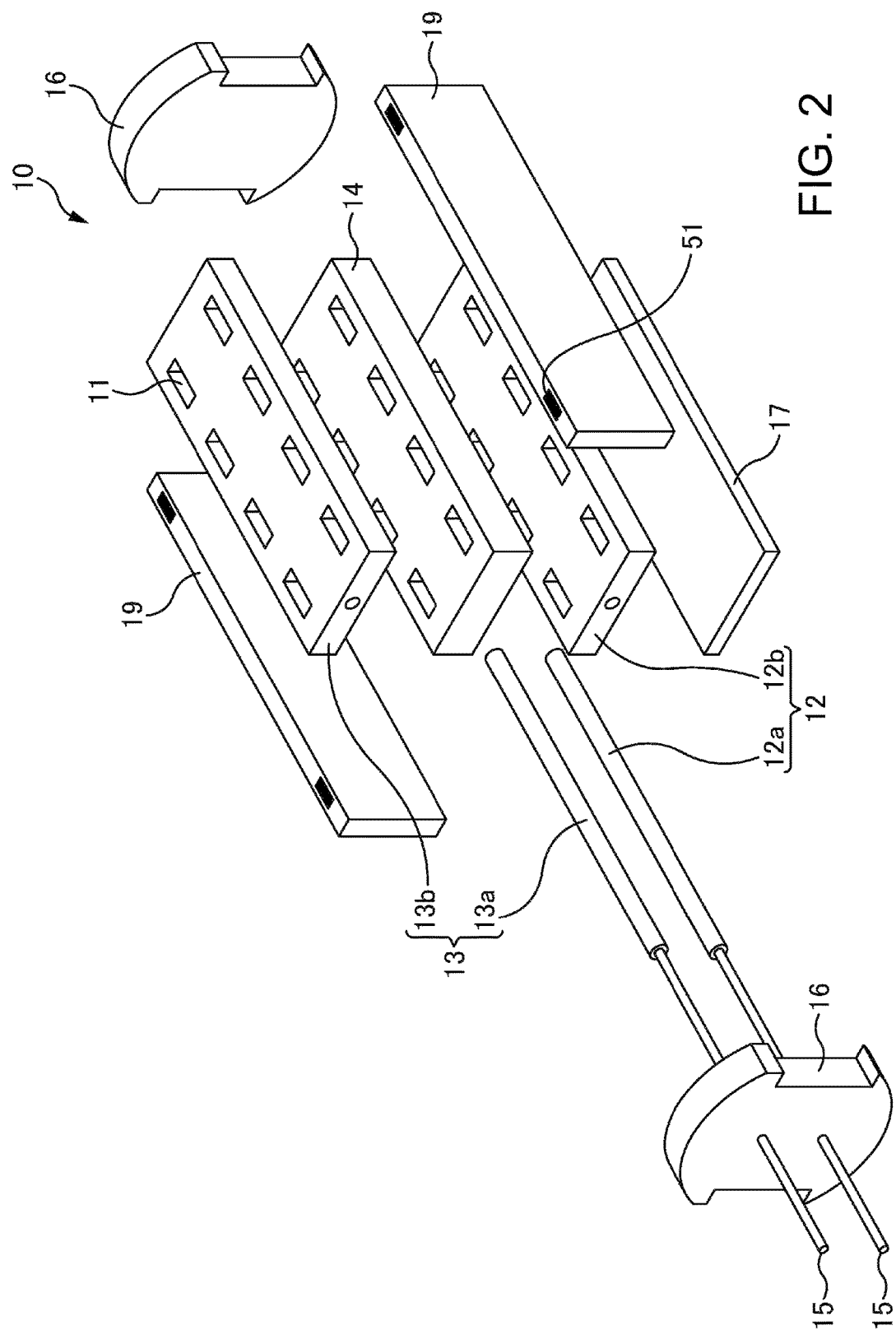
FIG. 2 is an exploded perspective view of a main body of the nucleic acid amplification reaction apparatus according to the embodiment.
Figure 4A:
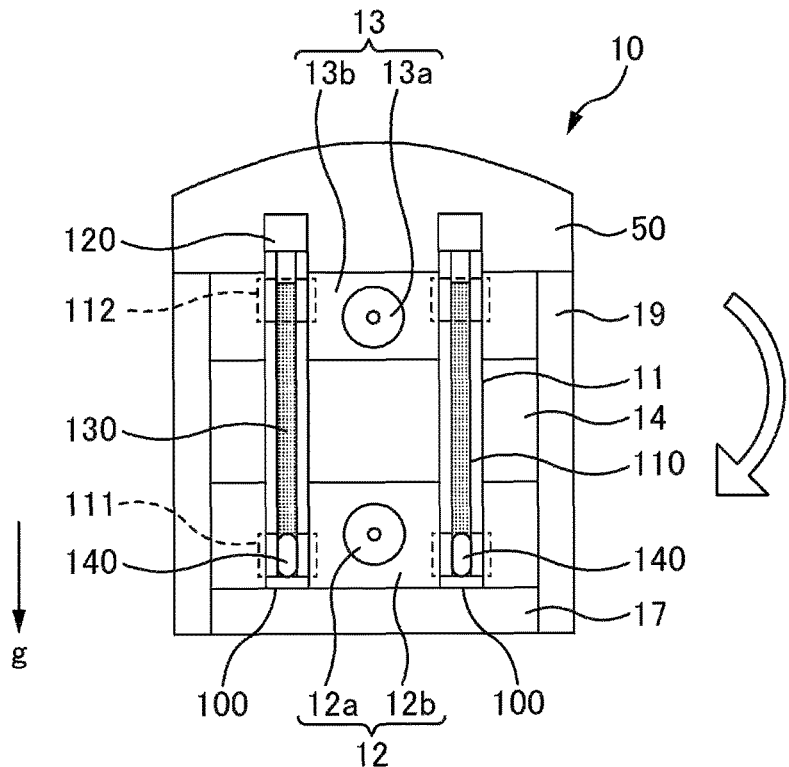

1-1. Configuration of Nucleic Acid Amplification Reaction Apparatus According to Embodiment FIGS. 1A and 1B are perspective views showing a nucleic acid amplification reaction apparatus 1 according to an embodiment. FIG. 1A shows a state in which a lid 50 of the nucleic acid amplification reaction apparatus 1 is closed and FIG. 1B shows a state in which the lid 50 of the nucleic acid amplification reaction apparatus 1 is opened and a nucleic acid amplification reaction vessel 100 is mounted in a mounting section 11. FIG. 2 is an exploded perspective view of a main body 10 of the nucleic acid amplification reaction apparatus 1 according to the embodiment. FIG. 4A is a cross-sectional view schematically showing a cross section of the main body 10 of the nucleic acid amplification reaction apparatus 1 according to the embodiment taken along line A-A in FIG. 1A.

As shown in FIG. 1A, the nucleic acid amplification reaction apparatus 1 according to the embodiment includes the main body 10 and a driving mechanism 20. As shown in FIG. 2, the main body 10 includes the mounting section 11, a first heating section 12 (corresponding to a heating section), and a second heating section 13. A spacer 14 is provided between the first heating section 12 and the second heating section 13. In the main body 10 of the embodiment, the first heating section 12 is arranged on the side of a bottom plate 17, and the second heating section 13 is arranged on the side of the lid 50. In the main body 10 of the embodiment, the first heating section 12, the second heating section 13, and the spacer 14 are fixed to a flange 16, the bottom plate 17, and a fixing plate 19.

The mounting section 11 is configured to mount the nucleic acid amplification reaction vessel 100, which will be described later. As shown in FIGS. 1B and 2, the mounting section 11 of the embodiment has a slot structure in which the nucleic acid amplification reaction vessel 100 is inserted and mounted, and is configured such that the nucleic acid amplification reaction vessel 100 is inserted into a hole penetrating through a first heat block 12b of the first heating section 12 (heating section), the spacer 14, and a second heat block 13b of the second heating section 13. The number of the mounting sections 11 may be more than one, and in the example shown in FIG. 1B, eight mounting sections 11 are provided in the main body 10.

Figure 4B:
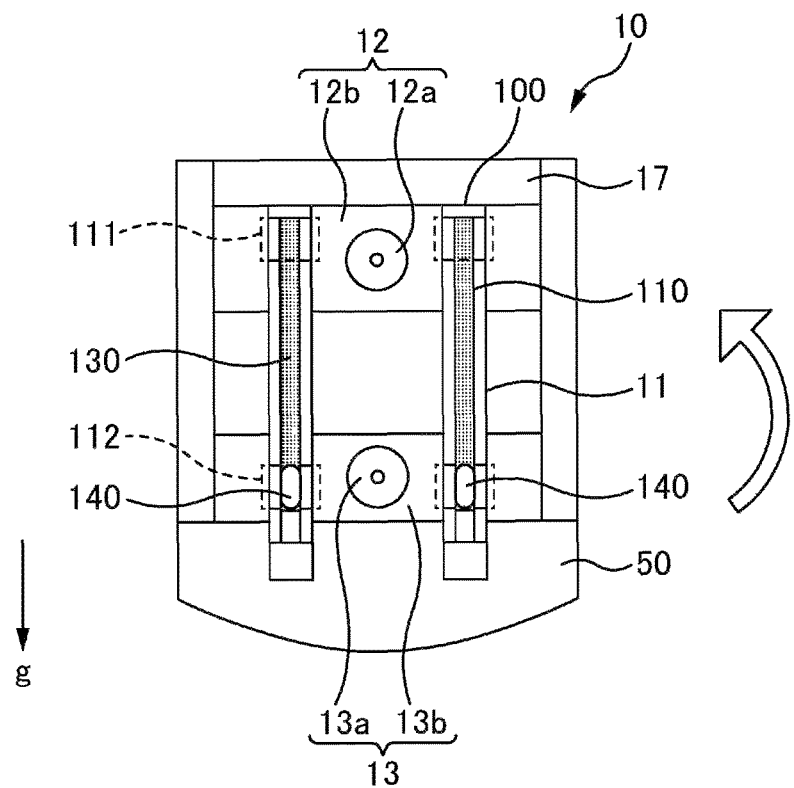

The nucleic acid amplification reaction apparatus 1 of the embodiment preferably includes a structure in which the nucleic acid amplification reaction vessel 100 is held at a predetermined position with respect to the first heating section 12 and the second heating section 13. Accordingly, a predetermined region of the nucleic acid amplification reaction vessel 100 can be heated by the first heating section 12 or the second heating section 13. More specifically, as shown in FIGS. 4A and 4B, in a flow channel 110 constituting the nucleic acid amplification reaction vessel 100, which will be described later, a first region 111 can be heated by the first heating section 12 and a second region 112 can be heated by the second heating section 13. In the embodiment, a structure that defines the position of the nucleic acid amplification reaction vessel 100 is the bottom plate 17, and as shown in FIG. 4A, by inserting the nucleic acid amplification reaction vessel 100 to a position in contact with the bottom plate 17, the nucleic acid amplification reaction vessel 100 can be held at a predetermined position with respect to the first heating section 12 and the second heating section 13.

When the nucleic acid amplification reaction vessel 100 is mounted in the mounting section 11, the first heating section 12 heats the first region 111 of the nucleic acid amplification reaction vessel 100, which will be described later, to a first temperature. In the example shown in FIG. 4A, in the main body 10, the first heating section 12 is arranged at a position for heating the first region 111 of the nucleic acid amplification reaction vessel 100.

The first heating section 12 may include a mechanism that generates heat and a member that transfers the generated heat to the nucleic acid amplification reaction vessel 100. In the example shown in FIG. 2, the first heating section 12 includes a first heater 12a and the first heat block 12b. In the embodiment, the first heater 12a is a cartridge heater, and is connected to an external power source (not shown) through a conductive wire 15. The first heater 12a is inserted into the first heat block 12b, and the first heat block 12b is heated by heat generated by the first heater 12a. The first heat block 12b is a member that transfers heat generated by the first heater 12a to the nucleic acid amplification reaction vessel 100. In the embodiment, the first heat block is an aluminum block.

Since the control of the temperature of the cartridge heater is easy, the temperature of the first heating section 12 can be easily stabilized by using the cartridge heater as the first heater 12a. Thus, a more accurate thermal cycle can be realized. Since the thermal conductivity of aluminum is high, by forming the first heat block 12b from aluminum, the nucleic acid amplification reaction vessel 100 can be efficiently heated. Further, since uneven heating of the first heat block 12b does not easily occur, a thermal cycle with high precision can be realized. In addition, since processing of aluminum is easy, the first heat block 12b can be molded with high precision and the precision of heating can be enhanced. Accordingly, a more accurate thermal cycle can be realized.

The first heating section 12 is preferably in contact with the nucleic acid amplification reaction vessel 100 when the nucleic acid amplification reaction vessel 100 is mounted in the mounting section 11. Accordingly, when the nucleic acid amplification reaction vessel 100 is heated by the first heating section 12, heat generated by the first heating section 12 can be stably transferred to the nucleic acid amplification reaction vessel 100, and thus, the temperature of the nucleic acid amplification reaction vessel 100 can be stabilized. In the case in which the mounting section 11 is formed as a part of the first heating section 12 as in the embodiment, the mounting section 11 preferably comes into contact with the nucleic acid amplification reaction vessel 100. Accordingly, heat generated by the first heating section 12 can be stably transferred to the nucleic acid amplification reaction vessel 100, and therefore, the nucleic acid amplification reaction vessel 100 can be efficiently heated.

When the nucleic acid amplification reaction vessel 100 is mounted in the mounting section 11, the second heating section 13 heats the second region 112 of the nucleic acid amplification reaction vessel 100 to a second temperature different from the first temperature. In the example shown in FIG. 4A, in the main body 10, the second heating section 13 is arranged at a position for heating the second region 112 of the nucleic acid amplification reaction vessel 100. As shown in FIG. 2, the second heating section 13 includes a second heater 13a and the second heat block 13b. The second heating section 13 is configured in the same manner as the first heating section 12 except that the region of the nucleic acid amplification reaction vessel 100 to be heated and the heating temperature are different from those for the first heating section 12.

In the embodiment, the temperatures of the first heating section 12 and the second heating section 13 are controlled by a temperature sensor (not shown) and a control section, which will be described later. The temperatures of the first heating section 12 and the second heating section 13 are preferably set so that the nucleic acid amplification reaction vessel 100 is heated to a desired temperature. In the embodiment, by controlling the first heating section 12 at the first temperature and the second heating section 13 at the second temperature, the first region 111 of the nucleic acid amplification reaction vessel 100 can be heated to the first temperature, and the second region 112 can be heated to the second temperature. The temperature sensor in the embodiment is a thermocouple.

The driving mechanism 20 is a mechanism that drives the mounting section 11, the first heating section 12, and the second heating section 13. Further, in the embodiment, the driving mechanism 20 includes a motor (not shown) and a drive shaft (not shown), and the drive shaft is connected to the flange 16 of the main body 10. The drive shaft in the embodiment is provided perpendicular to the longitudinal direction of the mounting section 11, and when the motor is operated, the main body 10 is rotated about the drive shaft as the axis of rotation.

The nucleic acid amplification reaction apparatus 1 of the embodiment includes the control section (not shown). The control section controls at least one of, for example, the first temperature, the second temperature, a first period, a second period, and the number of thermal cycles, which will be described later. In the case in which the control section controls the first period or the second period, the control section controls the operation of the driving mechanism 20, thereby controlling the period during which the mounting section 11, the first heating section 12, and the second heating section 13 are held in a predetermined arrangement. The control section may have mechanisms different in each item to be controlled, or may be a section which controls all items collectively.

The control section in the nucleic acid amplification reaction apparatus 1 of the embodiment is an electronic control system and controls all of the above-described items. The control section of the embodiment includes a processor such as a CPU (not shown) and a storage device such as an ROM (Read Only Memory) or an RAM (Random Access Memory). In the storage device, a variety of programs, data, and the like for controlling the above-described respective items are stored. In addition, the storage device has a work area for temporarily storing data during processing, processing results, and the like of various processes.

As shown in the example of FIGS. 2 and 4A, in the main body 10 of the embodiment, the spacer 14 is provided between the first heating section 12 and the second heating section 13. The spacer 14 of the embodiment is a member that holds the first heating section 12 or the second heating section 13. By providing the spacer 14, a distance between the first heating section 12 and the second heating section 13 can be more accurately determined. That is, the positions of the first heating section 12 and the second heating section 13 with respect to the first region 111 and the second region 112 of the nucleic acid amplification reaction vessel 100, which will be described later, can be more accurately determined.

The material of the spacer 14 can be appropriately selected as necessary, but is preferably a heat insulating material. Accordingly, effects of heat generated by the first heating section 12 and the second heating section 13, which mutually affect each other, can be reduced, and the control of the temperatures of the first heating section 12 and the second heating section 13 becomes easy. In the case in which the spacer 14 is made of a heat insulating material, when the nucleic acid amplification reaction vessel 100 is mounted in the mounting section 11, the spacer 14 is preferably arranged so as to surround the nucleic acid amplification reaction vessel 100 in a region between the first heating section 12 and the second heating section 13. Accordingly, the heat from the region between the first heating section 12 and the second heating section 13 of the nucleic acid amplification reaction vessel 100 can be prevented from being released, and thus, the temperature of the nucleic acid amplification reaction vessel 100 is further stabilized. In the embodiment, the spacer 14 is made of a heat insulating material, and in the example shown in FIG. 4A, the mounting section 11 penetrates through the spacer 14. Accordingly, when the nucleic acid amplification reaction vessel 100 is heated by the first heating section 12 and the second heating section 13, the heat of the nucleic acid amplification reaction vessel 100 is not easily released, and therefore, the temperatures of the first region 111 and the second region 112 can be further stabilized.

The main body 10 of the embodiment includes the fixing plate 19. The fixing plate 19 is a member that holds the mounting section 11, the first heating section 12, and the second heating section 13. In the example shown in FIGS. 1B and 2, two fixing plates 19 are fitted in the flanges 16, and the first heating section 12, the second heating section 13, and the bottom plate 17 are fixed. By the fixing plates 19, the strength of the structure of the main body 10 is increased, and therefore, the main body 10 is not easily damaged.

The nucleic acid amplification reaction apparatus 1 of the embodiment includes the lid 50. In the example shown in FIGS. 1A and 4A, the mounting section 11 is covered with the lid 50. By covering the mounting section 11 with the lid 50, when heating is performed by the first heating section 12, the release of heat from the main body 10 to the outside can be prevented, and therefore, the temperature in the main body 10 can be stabilized. The lid 50 may be fixed to the main body 10 by a fixing section 51. In the embodiment, the fixing section 51 is a magnet. As shown in the example of FIGS. 1B and 2, a magnet is provided on a surface of the main body 10 which comes into contact with the lid 50. Although not shown in FIGS. 1B and 2, a magnet is also provided for the lid 50 in a spot with which the magnet of the main body 10 comes into contact. When the mounting section 11 is covered with the lid 50, the lid 50 is fixed to the main body 10 with a magnetic force. Accordingly, the lid 50 can be prevented from moving or being detached from the main body when the main body 10 is driven by the driving mechanism 20. As a result, the temperature in the nucleic acid amplification reaction apparatus 1 can be prevented from changing due to the detachment of the lid 50. Thus, it is possible to subject a reaction solution 140, which will be described later, to a more accurate thermal cycle.

It is preferable that the main body 10 has a highly airtight structure. When the main body 10 has a highly airtight structure, the air in the main body 10 is not easily released to the outside of the main body 10. Thus, the temperature in the main body 10 is further stabilized. In the embodiment, as shown in FIG. 2, a space in the main body 10 is hermetically sealed by the two flanges 16, the bottom plate 17, the two fixing plates 19, and the lid 50.

It is preferable that the fixing plate 19, the bottom plate 17, the lid 50, and the flange 16 are formed using a heat insulating material. Accordingly, the heat from the main body 10 to the outside can be further prevented from being released. Therefore, the temperature in the main body 10 can be further stabilized.

Figure 3A:
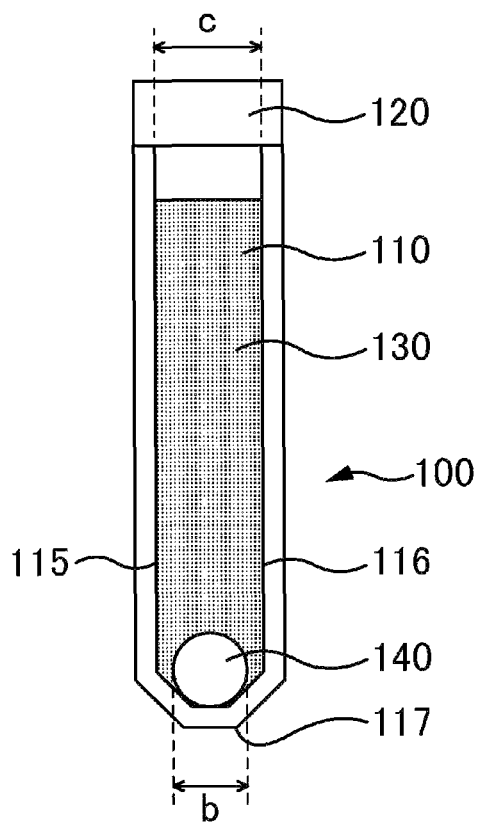
Figure 3B:
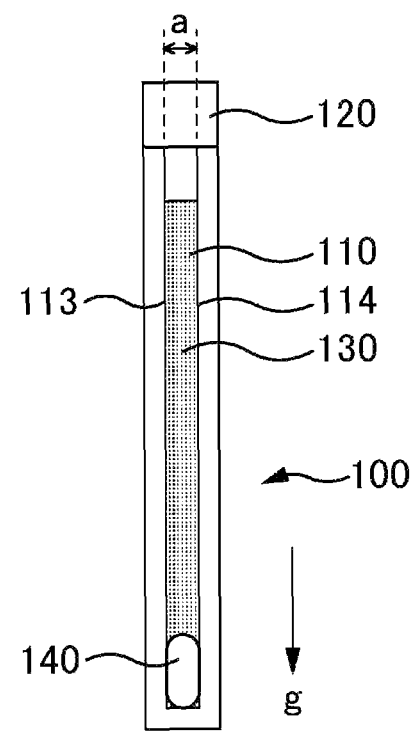
Figure 5:
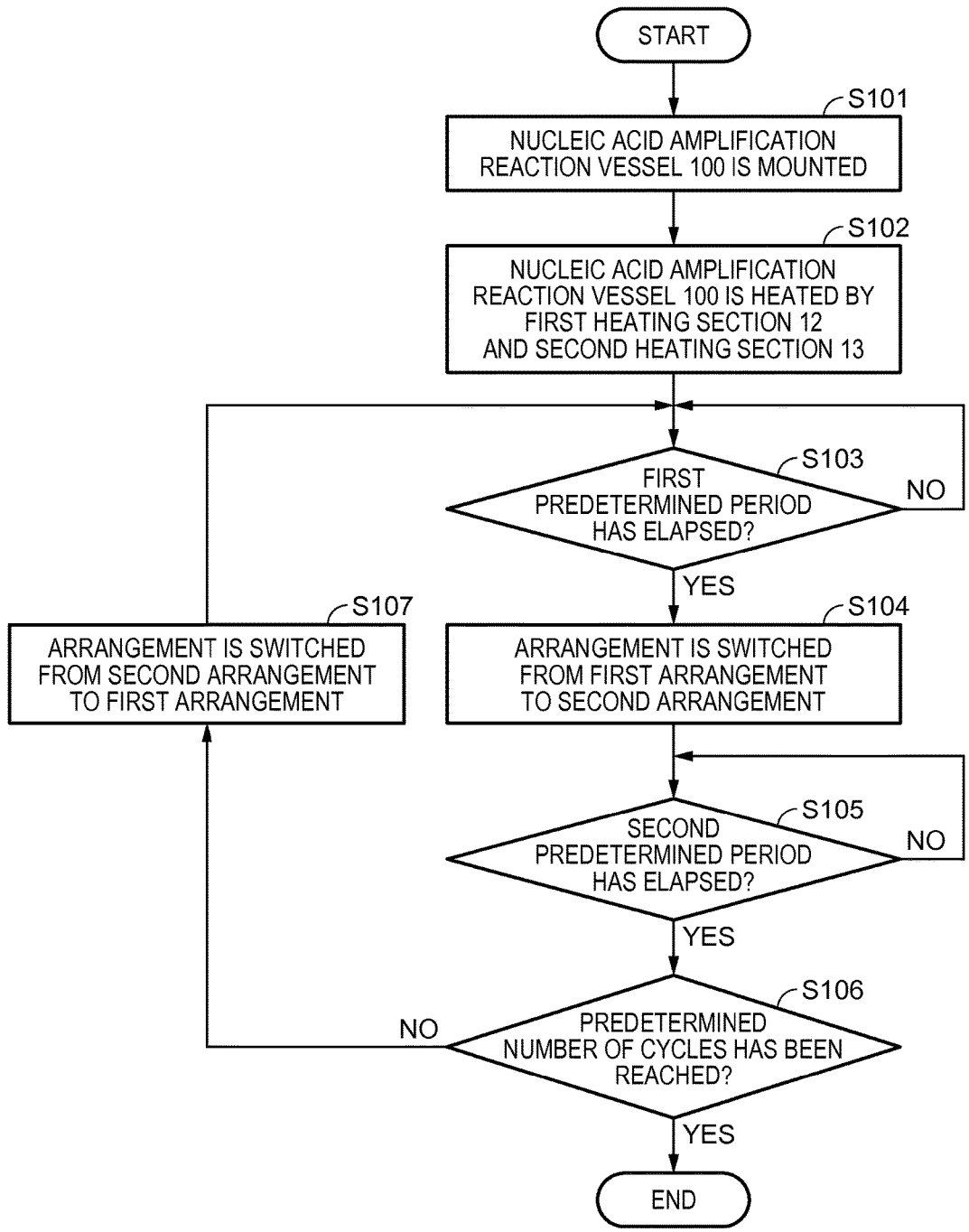
FIG. 5 is a flowchart showing a process procedure using the nucleic acid amplification reaction apparatus according to the embodiment.

1-2. Thermal Cycling Process Using Nucleic Acid Amplification Reaction Apparatus According to Embodiment FIGS. 3A and 3B are cross-sectional views of the nucleic acid amplification reaction vessel 100 according to the embodiment. FIGS. 4A and 4B are cross-sectional views schematically showing a cross section of the nucleic acid amplification reaction apparatus 1 according to the embodiment taken along line A-A in FIG. 1A. FIGS. 4A and 4B show states in which the nucleic acid amplification reaction vessel 100 is mounted on the nucleic acid amplification reaction apparatus 1. FIG. 4A shows a first arrangement and FIG. 4B shows a second arrangement. FIG. 5 is a flowchart showing a procedure of a thermal cycling process using the nucleic acid amplification reaction apparatus 1 according to the embodiment. Hereinafter, first, the nucleic acid amplification reaction vessel 100 according to the embodiment will be described and then, the thermal cycling process using the nucleic acid amplification reaction apparatus 1 according to the embodiment in the case of using the nucleic acid amplification reaction vessel 100 will be described.

As shown in the example of FIGS. 3A and 3B, the nucleic acid amplification reaction vessel 100 according to the embodiment includes a flow channel 110 and a sealing section 120. The flow channel 110 is filled with a reaction solution 140 and a liquid 130 which has a specific gravity smaller than the reaction solution 140 and is immiscible with the reaction solution 140 (hereinafter, referred to as "liquid") and sealed with the sealing section 120.

FIGS. 3A and 3B are cross-sectional views of the nucleic acid amplification reaction vessel 100 according to the embodiment, of which FIG. 3A is a cross-sectional view of the nucleic acid amplification reaction vessel 100 in a parallel direction with respect to the first inner wall 113 and the second inner wall 114 that are opposite to each other and FIG. 3B is a cross-sectional view of the nucleic acid amplification reaction vessel 100 in a direction orthogonal with respect to the first inner wall 113 and the second inner wall 114 (hereinafter, refers to as a "thickness direction"). The shape of the nucleic acid amplification reaction vessel 100 is flat and the flow channel 110 for moving the nucleic acid amplification reaction solution during the operation of the nucleic acid amplification reaction apparatus is formed in the direction along the center axis (vertical direction in FIGS. 3A and 3B). The nucleic acid amplification reaction vessel 100 is sealed with the sealing section 120. The center of a bottom section 170 of the nucleic acid amplification reaction vessel 100 is formed so as to protrude outward such that the droplet of the nucleic acid amplification reaction solution 140 put in the vessel is easily located at the center of the bottom section 170. The first inner wall 113 and the second inner wall 114 are flat. A distance between the first inner wall 113 and the second inner wall 114 (width a in FIG. 3B) is a length in which one droplet of the nucleic acid amplification reaction solution 140 that is poured into the nucleic acid amplification reaction vessel 100 comes into contact with both the first inner wall 113 and the second inner wall 114 at the same time. For example, when 1 µl to 7 µl of the nucleic acid amplification reaction solution 140 is poured, the distance between the first inner wall 113 and the second inner wall 114 is preferably 0.2 mm to 1.4 mm, and more preferably 0.2 mm to 0.8 mm. In addition, a distance between a third inner wall 115 and a fourth inner wall 116, which are inner walls of the side surfaces opposite to each other, (width c in FIG. 3A) is a length in which one droplet of the nucleic acid amplification reaction solution 140 does not come into contact with both the third inner wall 115 and the fourth inner wall 116 at the same time, and is preferably twice or more the diameter of the droplet when seen from the thickness direction of the nucleic acid amplification reaction vessel 100, and more preferably three times or more the diameter of the droplet so that the movement of the droplet of the nucleic acid amplification reaction solution 140 in the flow channel 110 in the longitudinal direction is not disturbed.

When the nucleic acid amplification reaction vessel 100 according to the embodiment is used, in the case in which the nucleic acid amplification reaction solution 140 moves in the longitudinal direction of the nucleic acid amplification reaction vessel 100, the nucleic acid amplification reaction solution 140 constantly comes into contact with both opposed inner walls of the nucleic acid amplification reaction vessel 100. Thus, the movement of the nucleic acid amplification reaction solution 140 in the direction perpendicular to the inner walls is limited and thus unevenness in a speed at which the nucleic acid amplification reaction solution moves is suppressed and the nucleic acid can be stably amplified.

In addition, in the nucleic acid amplification reaction vessel 100 according to the embodiment, since the fall position of the nucleic acid amplification reaction solution 140 is stabilized in the thickness direction of the nucleic acid amplification reaction vessel 100, as shown in the following Modification Example 1, fluorescence measurement for the nucleic acid amplification reaction solution 140 from a horizontal direction is easily achieved. In the related art, fluorescence measurement for the nucleic acid amplification reaction vessel from a downward direction is performed, but impurities for blocking light may be settled on the bottom of the nucleic acid amplification reaction vessel. Therefore, when fluorescence measurement from the horizontal direction is performed, more accurate measurement may be performed.

The amount of the droplet of the nucleic acid amplification reaction solution 140 poured is preferably 1.5 µl or more, and the distance between the first inner wall 113 and the second inner wall 114 (width a in FIG. 3B) is preferably 0.6 mm or less. Under the condition, as shown in examples, the nucleic acid amplification reaction solution 140 is interposed between the first inner wall 113 and the second inner wall 114 of the nucleic acid amplification reaction vessel 100 and the droplet of the nucleic acid amplification reaction solution 140 is compressed in the thickness direction, and the size thereof is enlarged in a direction orthogonal to the thickness direction. Accordingly, the diameter b of the droplet when seen from the thickness direction of the nucleic acid amplification reaction vessel is larger than the diameter of the droplet when the shape of the droplet is spherical in the case in which there is no compression effect by the first inner wall 113 and the second inner wall 114. Since the heat generated by the heating section is directly transferred to the nucleic acid amplification reaction solution 140 from the wall surfaces of the nucleic acid amplification reaction vessel 100 in a wide area without an oil, the heat transfer efficiency is high.

The first region 111 of the nucleic acid amplification reaction vessel 100 is apart of the flow channel 110 which is heated to the first temperature by the first heating section 12. The second region 112 is a part of the flow channel 110 which is different from the first region 111 and is heated to the second temperature by the second heating section 13. In the nucleic acid amplification reaction vessel 100 of the embodiment, the first region 111 is a region including one end portion in the longitudinal direction of the flow channel 110, and the second region 112 is a region including the other end portion in the longitudinal direction of the flow channel 110. In the example shown in FIGS. 4A and 4B, a region surrounded by the dotted line including an end portion on the proximal side of the sealing section 120 of the flow channel 110 is the second region 112, and a region surrounded by the dotted line including an end portion on the distal side of the sealing section 120 is the first region 111.

The flow channel 110 is filled with the liquid 130 and the reaction solution 140. Since the liquid 130 is immiscible with the reaction solution 140, that is, has properties such that the liquid is not mixed with the reaction solution, the reaction solution 140 is held in a state of a liquid droplet in the liquid 130 as shown in FIGS. 3A and 3B. The reaction solution 140 is located in the lowermost portion of the flow channel 110 with respect to the gravitational direction because the reaction solution has a specific gravity greater than the liquid 130. As the liquid 130, for example, dimethyl silicone oil or paraffin oil can be used. The reaction solution 140 is a liquid containing components required for a reaction. When the reaction is PCR, the reaction solution contains a DNA (a target nucleic acid) to be amplified by PCR, a DNA polymerase required for amplifying the DNA, a primer, and the like. For example, when performing PCR using an oil as the liquid 130, the reaction solution 140 is preferably an aqueous solution containing the above-described components.

Hereinafter, with reference to FIGS. 4A, 4B, and 5, the thermal cycling process using the nucleic acid amplification reaction apparatus 1 according to the embodiment will be described. In FIGS. 4A and 4B, the direction indicated by the arrow g (in the downward direction in the drawing) is the gravitational direction. In the embodiment, a case where shuttle PCR (two-stage temperature PCR) is performed will be described as an example of the thermal cycling process. The respective processes described below are shown as an example of a thermal cycling process, and according to the need, the order of the processes may be changed, two or more processes may be performed continuously or concurrently, or a process may be added.

The shuttle PCR is a method of amplifying a nucleic acid in a reaction solution by subjecting the reaction solution to a two-stage temperature process repeatedly between a high temperature and a low temperature. In the process at a high temperature, denaturation of a double-stranded DNA is performed and in the process at a low temperature, annealing (a reaction in which a primer is bound to a single-stranded DNA) and an extension reaction (a reaction in which a complementary strand to the DNA is formed by using the primer as a starting point) are performed.

In general, in the shuttle PCR, the high temperature is a temperature between 80° C. and 100° C. and the low temperature is a temperature between 50° C. and 70° C. The processes at the respective temperatures are performed for a predetermined period, and a period of maintaining the reaction solution at a high temperature is generally shorter than a period of maintaining the reaction solution at a low temperature. For example, the period for the process at a high temperature may be about 1 second to 10 seconds, and the period for the process at a low temperature may be about 10 seconds to 60 seconds, or a period longer than the above range may be adopted depending on the condition of the reaction.

Since the appropriate period, temperature, and number of cycles (number of times of repetition of the process at a high temperature and the process at a low temperature) change depending on the type or amount of a reagent to be used, it is preferable to determine an appropriate protocol in consideration of the type of a reagent or the amount of the reaction solution 140 before performing the reaction.

First, the nucleic acid amplification reaction vessel 100 according to the embodiment is mounted in the mounting section 11 (Step S101). In the embodiment, the nucleic acid amplification reaction vessel 100, in which the reaction solution 140 is introduced into the flow channel 110 which is filled with the liquid 130, and thereafter the flow channel 110 is sealed with the sealing section 120, is mounted in the mounting section 11. The introduction of the reaction solution 140 can be performed using a micropipette, an ink jet dispenser, or the like. In a state in which the nucleic acid amplification reaction vessel 100 is mounted in the mounting section 11, the first heating section 12 is in contact with the nucleic acid amplification reaction vessel 100 at a position including the first region 111 and the second heating section 13 is in contact with the nucleic acid amplification reaction vessel 100 at a position including the second region 112. In the embodiment, as shown in FIG. 4A, by mounting the nucleic acid amplification reaction vessel 100 in contact with the bottom plate 17, the nucleic acid amplification reaction vessel 100 can be held at a predetermined position with respect to the first heating section 12 and the second heating section 13.

In the embodiment, the arrangement of the mounting section 11, the first heating section 12, and the second heating section 13 in Step S101 is the first arrangement. As shown in FIG. 4A, the first arrangement is an arrangement in which the first region 111 is on the lower side of the second region 112 with respect to the gravitational direction. In the embodiment, the first arrangement is an arrangement in which the first region 111 of the nucleic acid amplification reaction vessel 100 is located in the lowermost portion of the flow channel 110 with respect to the gravitational direction. Accordingly, when the mounting section 11, the first heating section 12, and the second heating section 13 are in a predetermined arrangement, the first region 111 is a part of the flow channel 110 located in the lowermost portion of the flow channel 110 with respect to the gravitational direction. Since the first region 111 is located in the lowermost portion of the flow channel 110 with respect to the gravitational direction in the first arrangement, the reaction solution 140 having a specific gravity larger than the liquid 130 is located in the first region 111. In the embodiment, after the nucleic acid amplification reaction vessel 100 is mounted in the mounting section 11, the mounting section 11 is covered with the lid 50, and then the nucleic acid amplification reaction apparatus 1 is operated. In the embodiment, when the nucleic acid amplification reaction apparatus 1 is operated, Step S102 and Step S103 are started.

In Step S102, the nucleic acid amplification reaction vessel 100 is heated by the first heating section 12 and the second heating section 13. The first heating section 12 and the second heating section 13 heat different regions of the nucleic acid amplification reaction vessel 100 to different temperatures. That is, the first heating section 12 heats the first region 111 to the first temperature, and the second heating section 13 heats the second region 112 to the second temperature. Accordingly, a temperature gradient in which the temperature gradually changes between the first temperature and the second temperature is formed between the first region 111 and the second region 112 of the flow channel 110. In the embodiment, the first temperature is a relatively high temperature among the temperatures suitable for the intended reaction in the thermal cycling process, and the second temperature is a relatively low temperature among the temperatures suitable for the intended reaction in the thermal cycling process. Therefore, in Step S102 in the embodiment, a temperature gradient in which the temperature is decreased from the first region 111 to the second region 112 is formed. Since the thermal cycling process in the embodiment is the shuttle PCR, the first temperature is preferably a temperature suitable for the denaturation of a double-stranded DNA, and the second temperature is preferably a temperature suitable for the annealing and the extension reaction.

Since the arrangement of the mounting section 11, the first heating section 12, and the second heating section 13 in Step S102 is the first arrangement, when the nucleic acid amplification reaction vessel 100 is heated in Step S102, the reaction solution 140 is heated to the first temperature. Therefore, in Step S102, the reaction at the first temperature is performed for the reaction solution 140.

In Step S103, it is determined whether or not the first period has elapsed in the first arrangement. In the embodiment, the determination is performed by the control section (not shown). The first period is a period in which the mounting section 11, the first heating section 12, and the second heating section 13 are held in the first arrangement. In the embodiment, when Step S103 is performed subsequent to the mounting in Step S101, that is, when the first Step S103 is performed, it is determined whether or not the period from when the nucleic acid amplification reaction apparatus 1 is operated has reached the first period. Since the reaction solution 140 is heated to the first temperature in the first arrangement, the first period is preferably defined as a period in which the reaction solution 140 is subjected to the reaction at the first temperature in the intended reaction. In the embodiment, the first period is preferably defined as a period required for the denaturation of a double-stranded DNA.

In Step S103, when it is determined that the first period has elapsed (yes), the process proceeds to Step S104. When it is determined that the first period has not elapsed (no), Step S103 is repeated.

In Step S104, the main body 10 is driven by the driving mechanism 20, and the arrangement of the mounting section 11, the first heating section 12, and the second heating section is switched from the first arrangement to the second arrangement. The second arrangement is an arrangement in which the second region 112 is on the lower side of the first region 111 with respect to the vertical direction. In the embodiment, the second arrangement is an arrangement in which the second region 112 is located in the lowermost portion of the flow channel 110 with respect to the gravitational direction. In other words, the second region 112 is a region located in the lowermost portion of the flow channel 110 with respect to the gravitational direction when the mounting section 11, the first heating section 12, and the second heating section 13 are in a predetermined arrangement different from the first arrangement.

In Step S104 of the embodiment, the arrangement of the mounting section 11, the first heating section 12, and the second heating section 13 is switched from the state in FIG. 4A to the state in FIG. 4B. In the nucleic acid amplification reaction apparatus 1 of the embodiment, by the control of the control section, the driving mechanism 20 rotatively drives the main body 10. When the flanges 16 are rotatively driven by the motor by using the drive shaft as the axis of rotation, the mounting section 11, the first heating section 12, and the second heating section 13 which are fixed to the flanges 16 are rotated. Since the drive shaft is a shaft extending in the direction perpendicular to the longitudinal direction of the mounting section 11, when the drive shaft is rotated by the operation of the motor, the mounting section 11, the first heating section 12, and the second heating section 13 are rotated. In the example shown in FIGS. 4A and 4B, the main body 10 is rotated by 180°. Then, the arrangement of the mounting section 11, the first heating section 12, and the second heating section 13 is switched from the first arrangement to the second arrangement.

In Step S104, since the positional relationship between the first region 111 and the second region 112 with respect to the gravitational direction is opposite from that of the first arrangement, the reaction solution 140 moves from the first region 111 to the second region 112 by the gravitational force. After the arrangement of the mounting section 11, the first heating section 12, and the second heating section 13 has reached the second arrangement, when the control section stops the operation of the driving mechanism 20, the mounting section 11, the first heating section 12, and the second heating section 13 are held in the second arrangement. After the arrangement of the mounting section 11, the first heating section 12, and the second heating section 13 has reached the second arrangement, Step S105 is started.

In Step S105, it is determined whether or not the second period has elapsed in the second arrangement. The second period is a period in which the mounting section 11, the first heating section 12, and the second heating section 13 are held in the second arrangement. In the embodiment, since the second region 112 has been heated to the second temperature in Step S102, in Step S105 of the embodiment, it is determined whether or not the second period has been reached from when the arrangement of the mounting section 11, the first heating section 12, and the second heating section 13 has reached the second arrangement. In the second arrangement, the reaction solution 140 is held in the second region 112, and thus, the reaction solution 140 is heated to the second temperature during a period in which the main body 10 is held in the second arrangement. Accordingly, the second period is preferably defined as a period in which the reaction solution 140 is heated to the second temperature in the intended reaction. In the embodiment, the second period is preferably defined as a period required for the annealing and the extension reaction.

In Step S105, when it is determined that the second period has elapsed (yes), the process proceeds to Step S106. When it is determined that the second period has not elapsed (no), Step S105 is repeated.

In Step S106, it is determined whether or not the number of thermal cycles has reached a predetermined number of cycles. Specifically, it is determined whether or not the procedure from Step S103 to Step S105 has been performed a predetermined number of times. In the embodiment, the number of times that the procedure from Step S103 to Step S105 is completed is determined based on the number of times that a determination of "yes" is made. When the procedure from Step S103 to Step S105 is performed once, the reaction solution 140 is subjected to the thermal cycle once, and thus, the number of times that the procedure from Step S103 to Step S105 is performed can be used as the number of thermal cycles. Accordingly, in Step S106, it can be determined whether or not the thermal cycle has been performed a necessary number of times required for the intended reaction.

In Step S106, when it is determined that the thermal cycle has been performed a predetermined number of times (yes), the process is completed (END). When it is determined that the thermal cycle has not been performed a predetermined number of times (no), the process proceeds to Step S107.

In Step S107, the arrangement of the mounting section 11, the first heating section 12, and the second heating section 13 is switched from the second arrangement to the first arrangement. When the main body 10 is driven by the driving mechanism 20, the arrangement of the mounting section 11, the first heating section 12, and the second heating section 13 can be switched to the first arrangement. After the arrangement of the mounting section 11, the first heating section 12, and the second heating section 13 has reached the first arrangement, Step S103 is started.

When Step S103 is performed subsequent to Step S107, that is, in Step S103 for the second time and subsequent times, it is determined whether or not the first period has been reached from when the arrangement of the mounting section 11, the first heating section 12, and the second heating section 13 has reached the first arrangement.

The direction of the rotation of the mounting section 11, the first heating section 12, and the second heating section 13 by the driving mechanism 20 is preferably the opposite direction of the rotation in Step S104 and the rotation in Step S107. Accordingly, since twist generated in wires such as the conductive wire 15 is eliminated by rotation, wire deterioration can be suppressed. The rotation direction is preferably inversed in every operation by the driving mechanism 20. Then, compared to a case in which plural times of rotations in the same direction are performed, the degree of wire twisting can be reduced.

2. Modification Examples

Figure 7:
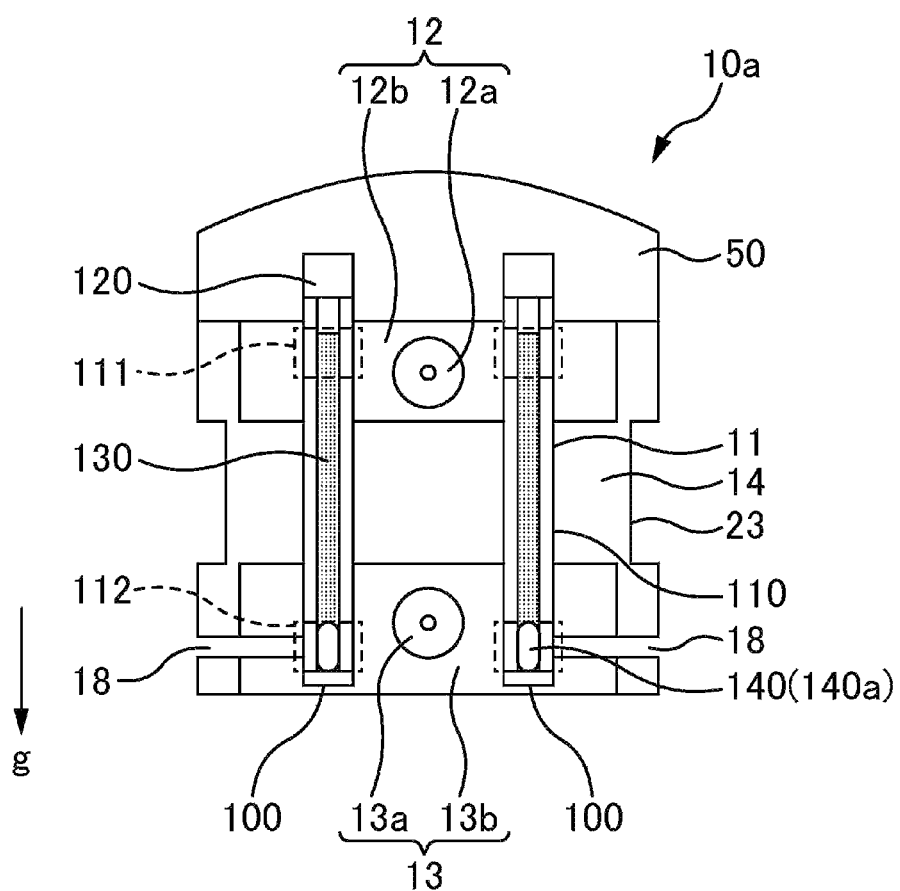
FIG. 7 is a cross-sectional view schematically showing a cross section of a main body of the nucleic acid amplification reaction apparatus according to the modification example taken along line B-B in FIG. 6A.

Hereinafter, modification examples will be described based on the embodiment. FIGS. 6A and 6B are perspective views showing a nucleic acid amplification reaction apparatus 2 according to a modification example, of which FIG. 6A shows a state in which a lid 50 is closed and FIG. 6B shows a state in which the lid 50 is opened. FIG. 7 is a cross-sectional view schematically showing a cross section of a main body 10a of the nucleic acid amplification reaction apparatus 2 according to the modification example taken along line B-B in FIG. 6A. The following modification examples can be arbitrarily combined as long as their configurations are consistent with each other, and the nucleic acid amplification reaction apparatus 2 shown in FIGS. 6A to 7 is an example of combining the configurations of Modification Examples 1, 4, 16, and 17. These modification examples will be described with reference to FIGS. 6A to 7.

In the following description, components different from those of the embodiment will be described in detail, and the same components as those of the embodiment will be denoted by the same reference signs and the description thereof will be omitted.

Modification Example 1

In the embodiment, the example in which the nucleic acid amplification reaction apparatus 1 does not include a detection device is shown. However, as shown in FIGS. 6A and 6B, the nucleic acid amplification reaction apparatus 2 according to this modification example may include a fluorescence detector 40 for measuring the amount of nucleic acid through the side wall of the second region 112 of the nucleic acid amplification reaction vessel. Accordingly, the nucleic acid amplification reaction apparatus 2 can be used in, for example, an analysis accompanied with fluorescence detection such as real-time PCR. The number of the fluorescence detectors 40 is arbitrary as long as the detection can be performed without any problems. In this modification example, a single fluorescence detector 40 is moved along a slide 22 to perform fluorescence detection. In order to perform fluorescence detection, a hole is provided on the side surface portion of the second heating section 13 of the main body 10a and a measurement window 18 (refer to FIGS. 6A to 7) is formed. When the nucleic acid amplification reaction solution is located in the second region 112, the fluorescence detector 40 emits excitation light to the side wall of the second region 112 of the nucleic acid amplification reaction vessel through the measurement window 18 and the amount of fluorescence radiated is measured. Then, the amount of nucleic acid amplified in the nucleic acid amplification reaction solution 140 can be measured.

In the modification example, in the nucleic acid amplification reaction apparatus 2 shown in FIGS. 6A to 7, the first heating section 12 is provided on the proximal side of the lid 50 and the second heating section 13 is provided on the distal side of the lid 50. That is, the positional relationship among the first heating section 12, the second heating section 13, and the other members included in the main body 10 is different from that of the nucleic acid amplification reaction apparatus 1. The functions of the first heating section 12 and the second heating section 13 are the same as in the first embodiment except that the positional relationship is different. In this modification example, as shown in FIG. 7, the measurement window 18 is provided on the side surface of the second heating section 13. Accordingly, in the real-time PCR in which fluorescence measurement is performed on the side of a low temperature (a temperature at which annealing and an extension reaction are performed), the fluorescence measurement can be appropriately performed.

Modification Example 2

In the embodiment, the first temperature and the second temperature are set to be a constant value throughout the thermal cycling process. However, at least one of the first temperature and the second temperature may be changed during the process. The first temperature and the second temperature can be changed by the control from the control section. By changing the arrangement of the first heating section 12 and the mounting section 11 to move the reaction solution 140, the reaction solution 140 can be heated to the changed temperature. Accordingly, for example, a reaction which requires a combination of two or more temperatures such as reverse transcription-PCR can be performed without increasing the number of the heating sections or making the structure of the apparatus complicated.

Modification Example 3

In the embodiment, the example in which the mounting section 11 has a slot structure is shown. However, the structure of the mounting section 11 may be any structure as long as the mounting section 11 can hold the nucleic acid amplification reaction vessel 100. For example, a structure in which the nucleic acid amplification reaction vessel 100 is fitted into a recess formed to be fitted for the shape of the nucleic acid amplification reaction vessel 100 or a structure in which the nucleic acid amplification reaction vessel 100 is held by pinching may be adopted.

Modification Example 4

In the embodiment, the structure that defines the position of the nucleic acid amplification reaction vessel 100 is the bottom plate 17. However, the structure that defines the position may be any structure as long as the nucleic acid amplification reaction vessel 100 can be held at a desired position. The structure that defines the position may be a structure provided in the nucleic acid amplification reaction apparatus 1 or a structure provided in the nucleic acid amplification reaction vessel 100 or a combination of both. For example, a screw, a plug-in stick, a structure in which a protrusion is provided in the nucleic acid amplification reaction vessel 100, or a structure in which the mounting section 11 and the nucleic acid amplification reaction vessel 100 are engaged with each other can be adopted. In the case of using a screw or a stick, such a structure may be configured such that the position of the nucleic acid amplification reaction vessel 100 to be held can be adjusted according to the reaction condition of the thermal cycle, the size of the nucleic acid amplification reaction vessel 100, and the like by changing the length of the screw or the insertion length of the screw, or changing the insertion position of the stick.

Modification Example 5

In the embodiment, the example in which the first heating section 12 and the second heating section 13 are each a cartridge heater is shown. However, the first heating section 12 and the second heating section 13 may be any heating section as long as the first heating section 12 can heat the first region 111 to the first temperature and the second heating section 13 can heat the second region 112 to the second temperature. For example, as the first heating section 12 and the second heating section 13, a carbon heater, a sheet heater, an induction heater (IH), a Peltier device, a heating liquid, or a heating gas can be used. In addition, different heating mechanisms may be adopted as the first heating section 12 and the second heating section 13.

Modification Example 6

In the embodiment, the example in which the nucleic acid amplification reaction vessel 100 is heated by the first heating section 12 and the second heating section 13 is shown. However, a cooling section that cools the second region 112 may be provided instead of the second heating section 13. As the cooling section, for example, a Peltier device can be used. Accordingly, for example, even in the case in which the temperature of the second region 112 is not easily decreased due to heat from the first region 111 of the nucleic acid amplification reaction vessel 100, a desired temperature gradient can be formed in the flow channel 110. Further, for example, it is possible to subject the reaction solution 140 to a thermal cycle in which heating and cooling are repeated.

Modification Example 7

In the embodiment, the example in which the material of the first heat block 12b and the second heat block 13b is aluminum is shown. However, the material of the heat blocks can be selected in consideration of the condition such as thermal conductivity, heat retention, or processability. For example, a copper alloy may be used, or plural materials may be used in combination. Further, the first heat block 12b and the second heat block 13b may be made of a different material.

Modification Example 8

As shown in the embodiment, in the case in which the mounting section 11 is formed as a part of the first heating section 12, a mechanism for bringing the nucleic acid amplification reaction vessel 100 into close contact with the mounting section 11 may be provided. Such a mechanism may be any mechanism as long as it can bring at least a part of the nucleic acid amplification reaction vessel 100 into close contact with the mounting section 11. For example, with a spring provided in the main body 10 or the lid 50, the nucleic acid amplification reaction vessel 100 may be pressed against one of the wall surfaces of the mounting section 11. Accordingly, since heat of the first heating section 12 can be more stably transferred to the nucleic acid amplification reaction vessel 100, the temperature of the nucleic acid amplification reaction vessel 100 can be further stabilized.

Modification Example 9

In the embodiment, the example in which the temperatures of the first heating section 12 and the second heating section 13 are controlled to be substantially the same as the temperatures to which the nucleic acid amplification reaction vessel 100 is heated is shown. However, the control of the temperatures of the first heating section 12 and the second heating section 13 is not limited to the embodiment. The temperatures of the first heating section 12 and the second heating section 13 may be any temperature as long as the temperatures are controlled so that the first region 111 and the second region 112 of the nucleic acid amplification reaction vessel 100 are heated to a desired temperature. For example, by considering the material and the size of the nucleic acid amplification reaction vessel 100, the first region 111 and the second region 112 can be more accurately heated to a desired temperature.

Modification Example 10

In the embodiment, the example in which the driving mechanism 20 is a motor is shown. However, the driving mechanism 20 may be any mechanism as long as it is a mechanism capable of driving the mounting section 11, the first heating section 12, and the second heating section 13. In the case in which the driving mechanism 20 is a mechanism that rotates the mounting section 11, the first heating section 12, and the second heating section 13, it is preferable that the driving mechanism 20 can control the rotation speed to an extent that the temperature gradient of the liquid 130 is not destroyed by the centrifugal force. In addition, in order to eliminate twisting of a wiring, it is preferable that the driving mechanism 20 can reverse the rotation direction. As such a mechanism, for example, a handle, a spring, and the like can be adopted.

Modification Example 11

In the embodiment, the example in which the mounting section 11 is a part of the first heating section 12 is shown. However, the mounting section 11 and the first heating section may be separate members as long as the positional relationship between both members does not change when the driving mechanism 20 is operated. In the case in which the mounting section 11 and the first heating section 12 are separate members, both members are preferably fixed to each other directly or through another member. In addition, the mounting section 11 and the first heating section 12 may be driven by the same mechanism or by different mechanisms, but are preferably operated such that the positional relationship between both members is kept constant. Accordingly, when the driving mechanism 20 is operated, the positional relationship between the mounting section 11 and the first heating section 12 can be kept constant, and thus, a predetermined region of the nucleic acid amplification reaction vessel 100 can be heated to a predetermined temperature. Incidentally, in the case in which the mounting section 11, the first heating section 12, and the second heating section 13 are driven by different mechanisms, the different mechanisms are collectively referred to as the driving mechanism 20.

Modification Example 12

In the embodiment, the example in which the temperature sensor is a thermocouple is shown. However, for example, a resistance temperature detector or a thermistor may be used.

Modification Example 13

In the embodiment, the example in which the fixing section 51 is a magnet is shown. However, the fixing section 51 may be any fixing section as long as it can fix the lid 50 and the main body 10. For example, a hinge or a catch clip may be adopted.

Modification Example 14

In the embodiment, the direction of the drive shaft is set to be perpendicular to the longitudinal direction of the mounting section 11, but is arbitrary as long as it can switch the arrangement of the mounting section 11, the first heating section 12, and the second heating section 13 between the first arrangement and the second arrangement. In the case in which the driving mechanism 20 is a mechanism that rotatively drives the mounting section 11, the first heating section 12, and the second heating section 13, the arrangement of the mounting section 11, the first heating section 12, and the second heating section 13 can be switched by setting a straight line which is not in parallel with the longitudinal direction of the mounting section 11 as the axis of rotation.

Modification Example 15

In the embodiment, the example in which the control section is an electronic control system is shown. However, the control section that controls the first period and the second period (a period control section) can be any control section as long as it can control the first period and the second period. That is, the control section can be any control section as long as it can control the timing of operation and stopping of the driving mechanism 20. In addition, the control section that controls the number of thermal cycles (a cycle number control section) may be any control section as long as it can control the number of thermal cycles. As the period control section and the cycle number control section, for example, a physical mechanism or an electronic control mechanism, or a combination thereof can be adopted.

Modification Example 16

The nucleic acid amplification reaction apparatus may include a setting section 25 as shown in FIGS. 6A and 6B. The setting section 25 is a user interface (UI), and is a device that sets the condition of the thermal cycle. By operating the setting section 25, at least one of the first temperature, the second temperature, the first period, the second period, and the number of thermal cycles can be set. The setting section 25 and the control section are mechanically or electronically interlocked with each other, and the setting in the setting section 25 is reflected in the control of the control section. Accordingly, since the condition of the reaction can be changed, the reaction solution 140 can be subjected to a desired thermal cycle. The setting section 25 may be configured such that any one of the above-described items can be individually set, or that when, for example, one reaction condition is selected from previously registered plural reaction conditions, necessary items are automatically set. In the example shown in FIGS. 6A and 6B, the setting section 25 uses a button system, and by pushing a button among buttons provided for individual items, the reaction condition can be set.

Modification Example 17

The nucleic acid amplification reaction apparatus may include a display section 24 as shown in FIGS. 6A and 6B. The display section 24 is a display device, and displays various items of information relating to the nucleic acid amplification reaction apparatus. The display section 24 may display the condition set by the setting section 25 or the actual period or temperature during the thermal cycling process. For example, when the setting is performed, an input condition is displayed, and during the thermal cycling process, a temperature measured by the temperature sensor, an elapsed period in the first arrangement or the second arrangement, or the number of thermal cycles performed may be displayed. Further, when the thermal cycling process is completed, or when any abnormality occurs in the apparatus, the event may be displayed. Further, a voice guided notification may also be performed. By performing the display or the voice guided notification, a user of the apparatus can easily recognize the progress status or completion of the thermal cycling process.

Modification Example 18

In the embodiment, the liquid 130 is a liquid having a specific gravity smaller than the reaction solution 140. However, the liquid 130 may be any liquid as long as it is a liquid which is immiscible with the reaction solution 140 and has a specific gravity different from the reaction solution 140. For example, a liquid which is immiscible with the reaction solution 140 and has a specific gravity larger than the reaction solution 140 may be adopted. When the liquid 130 has a specific gravity larger than the reaction solution 140, the reaction solution 140 is located in the uppermost portion of the flow channel 110 with respect to the gravitational direction.

Modification Example 19

In the embodiment, the direction of rotation in Step S104 and the direction of rotation in Step S107 are opposite to each other. However, after the rotation in the same direction is performed plural times, the rotation in the opposite direction may be performed the same number of times. By doing this, twisting of a wiring can be eliminated, and thus, deterioration of the wiring can be reduced as compared with the case in which the rotation in the opposite direction is not performed.

Modification Example 20

The nucleic acid amplification reaction apparatus 1 according to the embodiment includes the first heating section 12 and the second heating section 13. However, the second heating section 13 may not be provided. That is, as the heating section, only the first heating section 12 may be provided. Accordingly, the number of members to be used can be reduced, and therefore, the production cost can be reduced.

In this modification example, by heating the first region 111 of the nucleic acid amplification reaction vessel 100 by the first heating section 12, a temperature gradient in which the temperature gradually decreases with distance from the first region 111 is formed in the nucleic acid amplification reaction vessel 100. Since the second region 112 is a region different from the first region 111, the temperature thereof is maintained at the second temperature which is lower than that of the first region 111. In this modification example, the second temperature is controlled by, for example, the design of the nucleic acid amplification reaction vessel 100, the properties of the liquid 130, the setting of the temperature of the first heating section 12, and the like.

In this modification example, by switching the arrangement of the mounting section 11 and the first heating section 12 between the first arrangement and the second arrangement by the driving mechanism 20, the reaction solution 140 can be moved between the first region 111 and the second region 112. Since the first region 111 and the second region 112 are maintained at different temperatures, it is possible to subject the reaction solution 140 to a thermal cycle.

When the second heating section 13 is not provided, the spacer 14 holds the first heating section 12. Accordingly, the position of the first heating section 12 in the main body 10 can be more accurately defined, and thus, the first region 111 can be more reliably heated. When the spacer 14 is made of a heat insulating material, the temperatures of the first region 111 and the second region 112 can be further stabilized by arranging the spacer 14 to surround the region of the nucleic acid amplification reaction vessel 100 other than the region to be heated by the first heating section 12.

The nucleic acid amplification reaction apparatus of the modification example may have a mechanism for keeping the temperature of the main body 10 constant. Accordingly, the temperature of the second region 112 of the nucleic acid amplification reaction vessel 100 is further stabilized, and thus, it is possible to subject the reaction solution 140 to a more accurate thermal cycle. As the mechanism for keeping the temperature of the main body 10 constant, for example, a thermoregulated bath can be used.

Modification Example 21

In the embodiment, the example in which the nucleic acid amplification reaction apparatus 1 includes the lid 50 is shown. However, the lid 50 may not be provided. Accordingly, the number of members to be used can be reduced, and thus, the production cost can be reduced.

Modification Example 22

In the embodiment, the example in which the nucleic acid amplification reaction apparatus 1 includes the spacer 14 is shown. However, the spacer 14 may not be provided. Accordingly, the number of members to be used can be reduced, and thus, the production cost can be reduced.

Modification Example 23

In the embodiment, the example in which the nucleic acid amplification reaction apparatus 1 includes the bottom plate 17 is shown. However, as shown in FIG. 7, the bottom plate 17 may not be provided. Accordingly, the number of members to be used can be reduced, and thus, the production cost can be reduced.

Modification Example 24

In the embodiment, the example in which the nucleic acid amplification reaction apparatus 1 includes the fixing plate 19 is shown. However, the fixing plate 19 may not be provided. Accordingly, the number of members to be used can be reduced, and thus, the production cost can be reduced.

Modification Example 25

In the embodiment, the example in which the spacer 14 and the fixing plate 19 are separate members is shown. However, as shown in FIG. 7, the spacer 14 and the fixing plate 19 may be integrally formed. Further, the bottom plate 17 and the spacer 14, or the bottom plate 17 and the fixing plate 19 may be integrally formed.

Modification Example 26

The spacer 14 and the fixing plate 19 may be transparent. Accordingly, when a transparent nucleic acid amplification reaction vessel 100 is used in the thermal cycling process, a manner in which the reaction solution 140 moves can be observed from the outside of the apparatus. As a result, it can be visually confirmed whether or not the thermal cycling process is appropriately performed. Therefore, the degree of the "transparency" in this case may be sufficient if the movement of the reaction solution 140 can be visually observed when the thermal cycling process is performed using these members in the nucleic acid amplification reaction apparatus 1.

Modification Example 27

In order to observe the inside of the nucleic acid amplification reaction apparatus 1, the nucleic acid amplification reaction apparatus may be configured such that the spacer 14 is made of a transparent material and the fixing plate 19 is omitted, or the fixing plate 19 is made of a transparent material and the spacer 14 is omitted, or both the spacer 14 and the fixing plate 19 are omitted. As the number of members present between an observer and the nucleic acid amplification reaction vessel 100 to be observed is decreased, the effect of the members on light refraction is decreased, and thus, it becomes easy to observe the inside. Further, as the number of members is small, the production cost can be reduced.

Modification Example 28

In order to observe the inside of the nucleic acid amplification reaction apparatus 1, as shown in FIGS. 6A to 7, an observation window 23 may be provided in the main body 10a. The observation window 23 may be, for example, a hole or a slit formed in the spacer 14 or the fixing plate 19. In the example shown in FIG. 7, the observation window 23 is a recess provided in the transparent spacer 14 integrally formed with the fixing plate 19. By providing the observation window 23, the thickness of the members existing between an observer and the nucleic acid amplification reaction vessel 100 to be observed can be decreased, and thus, it becomes easy to observe the inside.

Modification Example 29

In the embodiment, the example in which the first heating section 12 is arranged on the side of the bottom plate 17 of the main body 10, and the second heating section 13 is arranged on the side of the lid 50 is shown. However, as shown in FIG. 7, the first heating section 12 may be arranged on the side of the lid 50. In the case in which the first heating section 12 is arranged on the side of the lid 50, the arrangement of the mounting section 11, the first heating section 12, and the second heating section 13 when the nucleic acid amplification reaction vessel 100 is mounted in Step S101 in the embodiment is the second arrangement. That is, the second region 112 is located in the lowermost portion of the flow channel 110 with respect to the gravitational direction. Accordingly, in the case in which the nucleic acid amplification reaction apparatus 2 of the modification example is applied to the thermal cycling process according to the embodiment, when the nucleic acid amplification reaction vessel 100 is mounted in the mounting section 11, the arrangement is switched to the first arrangement. Specifically, before the process proceeds from Step S101 to Step S102 and Step S103, a process of Step S107 is performed.

Modification Example 30

In the embodiment, the example in which the process of heating the nucleic acid amplification reaction vessel 100 by the first heating section 12 and the second heating section 13 (Step S102) and the process of determining whether or not the first period has elapsed (Step S103) are started after the nucleic acid amplification reaction vessel 100 is mounted in the mounting section 11 (Step S101) is shown. However, the timing of starting Step S102 is not limited to the embodiment. Step S102 may be started at any timing as long as the first region 111 is heated to the first temperature by the time when the period measurement is started in Step S103. The timing of performing Step S102 is determined in consideration of the size or the material of the nucleic acid amplification reaction vessel 100 to be used, a period required for heating the first heat block 12b, or the like. For example, Step S102 may be started before Step S101, or concurrently with Step S101, or may be started after Step S101 and before Step S103.

Modification Example 31

In the embodiment, the example in which the first temperature, the second temperature, the first period, the second period, the number of thermal cycles, and the operation of the driving mechanism 20 are controlled by the control section is shown. However, a user can control at least one of these items. When a user controls the first temperature or the second temperature, for example, a temperature measured by the temperature sensor is displayed on the display section 24, and the user may adjust the temperature by operating the setting section 25. In the case in which a user controls the number of thermal cycles, the user stops the nucleic acid amplification reaction apparatus 1 when the number of thermal cycles has reached a predetermined number of cycles. The counting of the thermal cycles may be performed by the user or by the nucleic acid amplification reaction apparatus 1 and the number of thermal cycles may be displayed on the display section 24.

In the case where a user controls the first period or the second period, the user determines whether or not a predetermined period has been reached and causes the nucleic acid amplification reaction apparatus 2 to switch the arrangement of the mounting section 11, the first heating section 12, and the second heating section 13. That is, the user performs Step S103 and Step S105 and at least a part of Step S104 and Step S107 shown in FIG. 5. The period may be measured using a timer which is not interlocked with the nucleic acid amplification reaction apparatus 2 or the elapsed time may be displayed on the display section 24 of the nucleic acid amplification reaction apparatus 2. The switching of the arrangement may be performed by operating the setting section 25 (UI) or manually performed by employing a handle in the driving mechanism 20.

Modification Example 32

In the embodiment, the example in which the angle of rotation when the arrangement of the mounting section 11, the first heating section 12, and the second heating section 13 is switched by the rotation of the driving mechanism 20 is 180° is shown. However, the angle of rotation may be any angle as long as the vertical positional relationship between the first region 111 and the second region 112 with respect to the gravitational direction is changed. For example, when the angle of rotation is less than 180°, the speed of movement of the reaction solution 140 is decreased. Therefore, by adjusting the angle of rotation, the period in which the reaction solution 140 moves between the first temperature and the second temperature can be adjusted. That is, a period in which the temperature of the reaction solution 140 is changed between the first temperature and the second temperature can be adjusted.

EXAMPLES

The appropriate conditions for the distance between the first inner wall and the second inner wall of the nucleic acid amplification reaction apparatus according to the invention and the amount of the nucleic acid amplification reaction solution to be poured will be shown.

Figure 8:
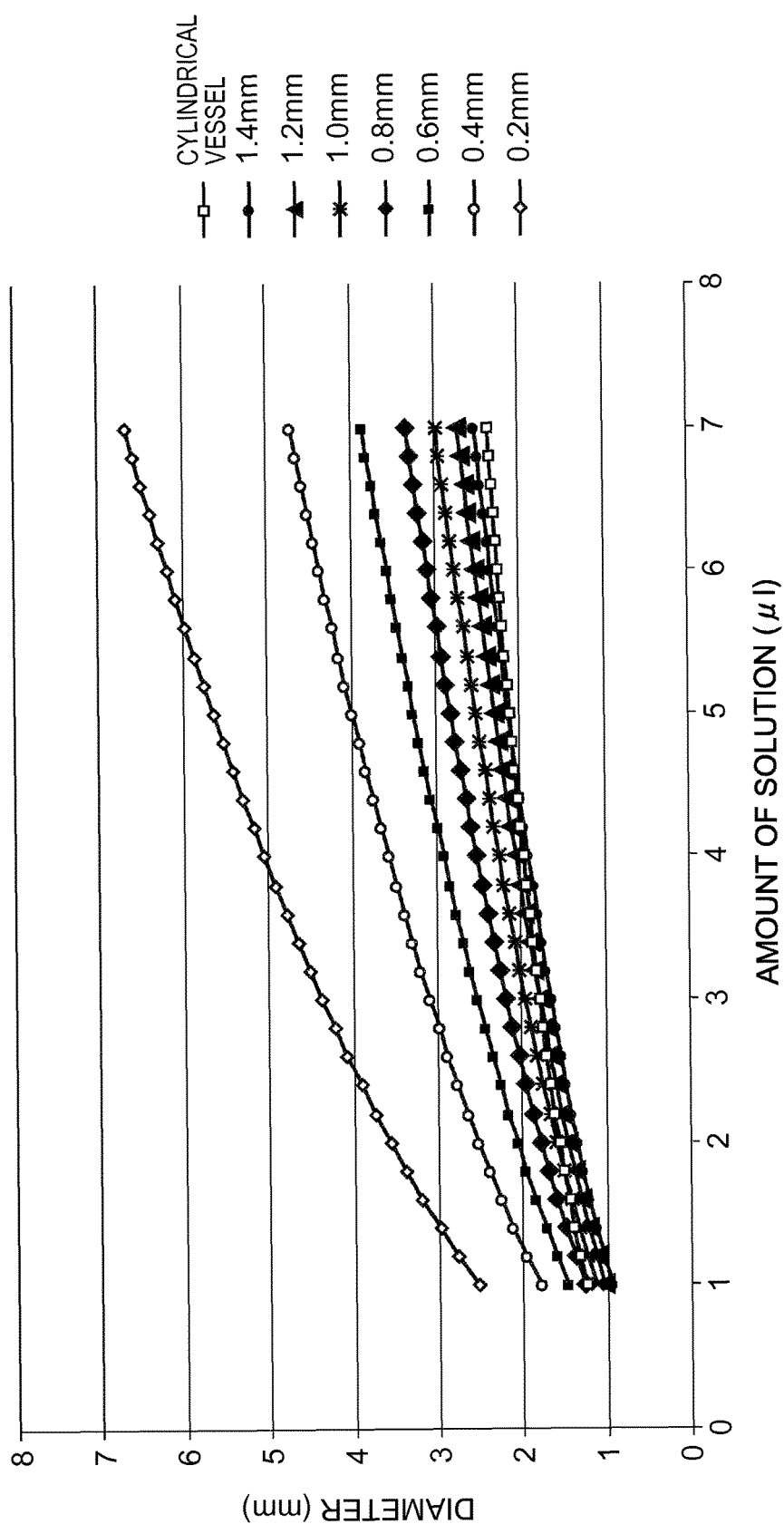
FIG. 8 is a graph showing sizes of projection diameters of droplets in a nucleic acid amplification reaction vessel.

Here, in the case in which the nucleic acid amplification reaction solution was poured, when the diameter of the droplet of the nucleic acid amplification reaction solution as seen in the thickness direction of the nucleic acid amplification reaction vessel was substantially calculated, it was considered that the shape of the droplet in the nucleic acid amplification reaction vessel was a columnar shape in which a portion of the droplet that came into contact with the first inner wall and the second inner wall had a circular bottom surface, and the width of the nucleic acid amplification reaction vessel (the interval between the first inner wall and the second inner wall) became the height. The diameter of the bottom surface thereof was considered as the diameter of the droplet of the nucleic acid amplification reaction solution. In addition, it was considered that the shape of the droplet of the nucleic acid amplification reaction solution when the nucleic acid amplification reaction solution was poured into the cylindrical nucleic acid amplification reaction vessel according to Comparative Example was a spherical shape. The diameter thereof was considered as the diameter of the droplet of the nucleic acid amplification reaction solution. In FIG. 8, the results of Examples and Comparative Example are shown. In FIG. 9, the results of obtaining ratios of Examples to Comparative Example are shown.

As shown in FIGS. 8 and 9, it is found that the diameter of the droplet was large in the case in which 1.0 µl to 7.0 µl of the nucleic acid amplification reaction solution was poured into each nucleic acid amplification reaction vessel in which the distance between the first inner wall and the second inner wall was 0.2 mm to 0.8 mm, compared to the case in which the droplet was poured into the cylindrical nucleic acid amplification reaction vessel.

The invention is not limited to the embodiment described above, and various modifications may be made. For example, the invention includes substantially the same configuration as the configuration described in the embodiment (for example, the configuration in which the function, the method, and the result are the same, or the configuration having the same object and the effect). The invention also includes configurations in which a portion which is not essential in the configuration described in the embodiment is replaced. The invention also includes configurations which achieve the same effects and advantages as the configuration described in the embodiment, or configurations which are able to achieve the same object. The invention also includes configurations including known techniques added to the configuration described in the embodiment.

The entire disclosure of Japanese Patent Application No. 2014-030362, filed Feb. 20, 2014 is expressly incorporated by reference herein.

What is claimed is:

1. A nucleic acid amplification reaction vessel comprising:
   a first inner wall;
   a second inner wall that is arranged opposite to the first inner wall, wherein a distance between the first inner wall and the second inner wall is a length shorter than a diameter b of a droplet of a nucleic acid amplification reaction solution, such that the droplet of nucleic acid amplification reaction solution comes into contact with both the first inner wall and the second inner wall, simultaneously, when the reaction vessel is filled with a liquid and the nucleic acid amplification reaction solution is loaded into the reaction vessel, wherein the liquid has a lower specific gravity than the nucleic acid amplification reaction solution such that the reaction solution forms the droplet having the diameter b within the liquid;
   a third inner wall; and
   a fourth inner wall that is arranged opposite to the third inner wall, the third inner wall and fourth inner wall being orthogonal to the first inner wall and the second inner wall, wherein a distance between the third inner wall and the fourth inner wall is a length at least twice the diameter b of the droplet of the nucleic acid amplification reaction solution, such that the droplet of the nucleic acid amplification reaction solution does not come into contact with both the third inner wall and the fourth inner wall at the same time when the nucleic acid amplification reaction solution is loaded into the reaction vessel filled with the liquid.

2. The nucleic acid amplification reaction vessel according to claim 1, wherein the first inner wall and the second inner wall are flat.

3. The nucleic acid amplification reaction vessel according to claim 1, wherein when an amount of the nucleic acid amplification reaction solution poured into the nucleic acid amplification reaction vessel is 1.0 µl to 7.0 µl, the distance between the inner surface of the first side wall and the inner surface of the second side wall is 0.2 mm to 1.4 mm.

4. The nucleic acid amplification reaction vessel according to claim 1, wherein a center portion of a bottom portion of the nucleic acid amplification reaction vessel protrudes outward from the peripheral portion.

5. A nucleic acid amplification reaction apparatus comprising:
   a mounting section, that is mountable the nucleic acid amplification reaction vessel according to claim 1;
   a first heating section that heats a first region of the nucleic acid amplification reaction vessel when the nucleic acid amplification reaction vessel is mounted in a mounting section; and
   a driving mechanism that switches arrangement of the first region, a second region of the nucleic acid amplification reaction vessel, and the first heating section into a first arrangement or a second arrangement,
   wherein the first arrangement is an arrangement in which the first region is on a lower side of the second region with respect to a gravitational direction, and
   the second arrangement is an arrangement in which the second region is on a lower side of the first region with respect to the gravitational direction.

6. The nucleic acid amplification reaction apparatus according to claim 5, wherein the nucleic acid amplification reaction apparatus includes a second heating section that heats the second region when the nucleic acid amplification reaction vessel is mounted in a mounting section,
   the first heating section heats the first region to a first temperature, and
   the second heating section heats the second region to a second temperature which is different from the first temperature.

7. A nucleic acid amplification reaction vessel comprising:
   a first inner wall;
   a second inner wall that is arranged opposite to the first inner wall, wherein a distance between the first inner wall and the second inner wall is a length shorter than a diameter b of a droplet of a nucleic acid amplification reaction solution, such that the droplet of the nucleic acid amplification reaction solution comes into contact with both the first inner wall and the second inner wall, simultaneously, when the reaction vessel is filled with a liquid and 1.0 µl to 7.0 µl of the nucleic acid amplification reaction solution is loaded into the reaction vessel, wherein the liquid has a lower specific gravity than the nucleic acid amplification reaction solution such that the reaction solution forms the droplet having the diameter b within the liquid;

a third inner wall; and a fourth inner wall that is arranged opposite to the third inner wall, the third inner wall and fourth inner wall being orthogonal to the first inner wall and the second inner wall, wherein a distance between the third inner wall and the fourth inner wall is a length at least twice the diameter b of the droplet of the nucleic acid amplification reaction solution, such that the droplet of the nucleic acid amplification reaction solution does not come into contact with both the third inner wall and the fourth inner wall at the same time when the 1.0 µl to 7.0 µl of the nucleic acid amplification reaction solution is loaded into the reaction vessel filled with the liquid.

8. The nucleic acid amplification reaction apparatus according to claim 7, wherein the distance between an inner surface of the first side wall and an inner surface of the second side wall is 0.2 mm to 1.4 mm.

\* \* \* \* \*